United States Patent [19]
Ellard

[11] Patent Number: 5,871,448
[45] Date of Patent: Feb. 16, 1999

[54] STEPPER APPARATUS FOR USE IN THE IMAGING/TREATMENT OF INTERNAL ORGANS USING AN ULTRASOUND PROBE

[75] Inventor: Terence R. Ellard, Seattle, Wash.

[73] Assignee: Real World Design and Development Co., Seattle, Wash.

[21] Appl. No.: 949,731

[22] Filed: Oct. 14, 1997

[51] Int. Cl.⁶ ..................................................... A61B 8/00

[52] U.S. Cl. ........................................... 600/459; 600/462

[58] Field of Search ................................... 600/463, 459, 600/444, 449, 461

[56] References Cited

U.S. PATENT DOCUMENTS

| | | | |
|---|---|---|---|
| 5,211,176 | 5/1993 | Ishiguro et al. | 600/463 |
| 5,282,472 | 2/1994 | Companion et al. | 600/459 |
| 5,361,768 | 11/1994 | Webler et al. | 600/463 |
| 5,474,071 | 12/1995 | Chapelon et al. | 600/459 |

OTHER PUBLICATIONS

Cotan Stabilizing Device, Mick Radio–Nuclear Instruments Inc., pp. 003–008, Dec. 12, 1996.

Stepping Unit UA 1084, Hutchinson Medical Designs, pp. 1–6, Oct. 1994.

*Primary Examiner*—Marvin M. Lateef
*Assistant Examiner*—Maulin Patel
*Attorney, Agent, or Firm*—Jensen & Puntigam, P.S.

[57] ABSTRACT

The stepper apparatus for use in imaging/treatment of prostate cancer with radioactive seeds includes a body portion, a support element for holding the ultrasound probe, a slide portion for moving the support element relative to the body portion, and a support element for holding a template which has a plurality of openings therethrough, through which radiation seed insertion needles may be positioned. The ultrasound probe may be moved longitudinally relative to the prostate in indexed steps of a known distance and also may be moved in a controlled, continuous fashion to determine the rear edge of the prostate which can then be used as a reference for future indexed steps. The slide portion moves along two spaced guide rods, one of which has a threaded portion which mates with a spring-loaded ball in the side of the slide portion as well as a rack and gear arrangement for accomplishing the dual (indexed and continuous) motion.

9 Claims, 3 Drawing Sheets

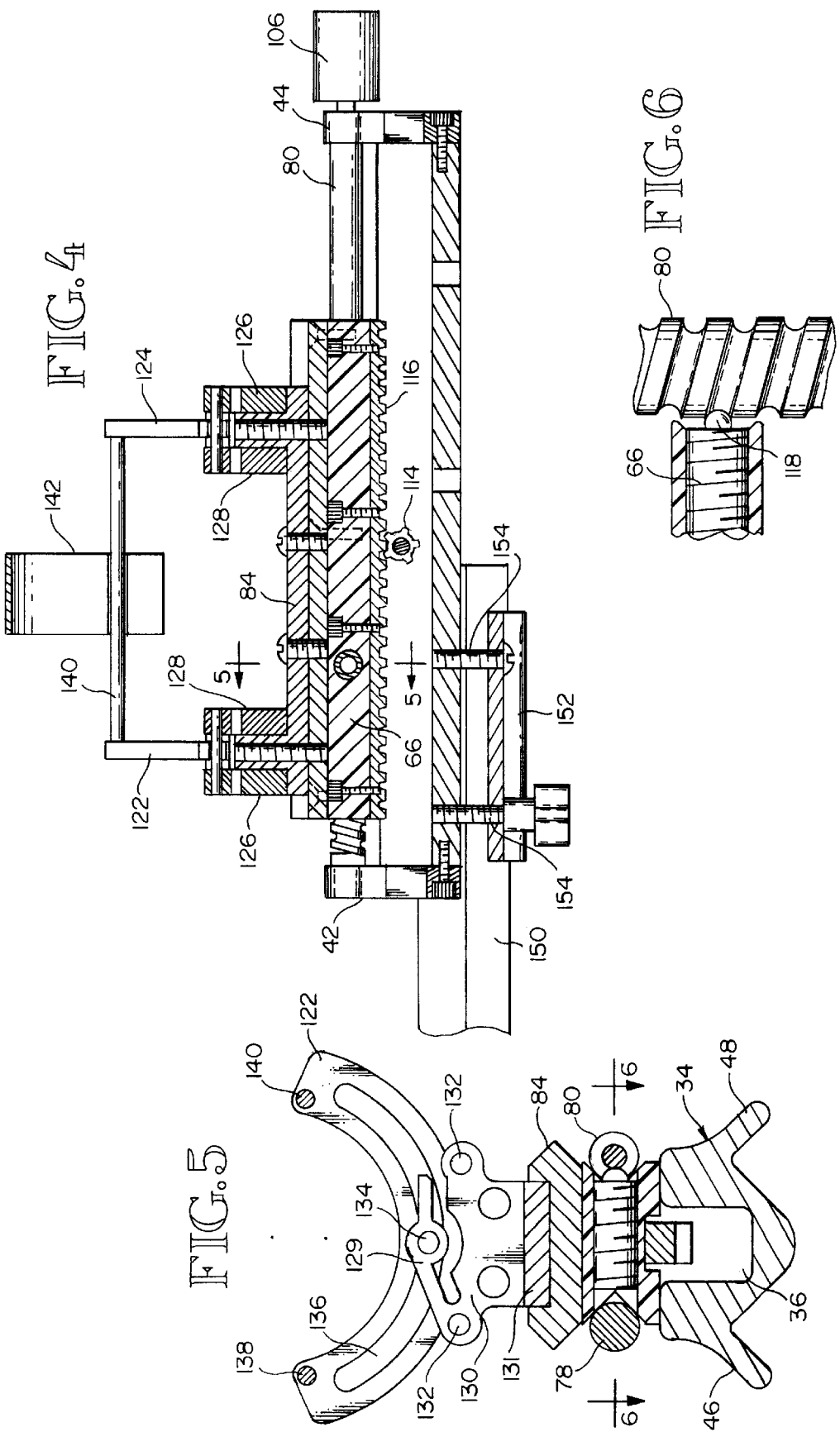

5,871,448

STEPPER APPARATUS FOR USE IN THE IMAGING/TREATMENT OF INTERNAL ORGANS USING AN ULTRASOUND PROBE

TECHNICAL FIELD

This invention relates generally to apparatus used in the imaging and/or treatment of internal organs and tissues, such as in radiation treatment for prostate cancer, and more specifically concerns a stepper apparatus for referencing and moving an ultrasound probe in a controlled manner for such imaging and treatment functions.

BACKGROUND OF THE INVENTION

This invention is particularly useful in the radiation treatment of prostate cancer, among other imaging/treatment applications, and prostate cancer is the focus of this application. It is well known that prostate cancer is a leading cause of death in males, and further that the chances of incurring prostate cancer increase significantly with age. It is also well known that prostate cancer is a complex disease and quite variable, since it can be slow-growing, and hence typically not life-threatening, or it can be very aggressive and fast growing. A number of tests have been developed to attempt to ascertain and differentiate between the slow growing prostate cancers and the significantly more aggressive ones; research continues in this area. It is the aggressive cancers which require prompt treatment; it is advantageous to eliminate the presence of these cancers from the body in the early stages of the cancer and as soon as possible after discovery.

In the treatment of prostate cancer, only a few options have been heretofore available. The most prevalent treatment has been complete removal of the prostate by means of a surgical procedure. However, as with other surgeries, such a procedure is invasive, requires a substantial amount of recovery time, and can have serious complications and side effects, including incontinence and/or impotence. Such serious side effects in many cases deter individuals from treatment or even regular screenings.

Other treatment techniques for prostate cancer include radiation therapy by an externally transmitted beam, which has not proven to be as effective as surgery, and radiation therapy which involves the placement of small radioactive particles, referred to as "seeds", within the prostate. This treatment has proven to be increasingly effective, approximately the same as surgery, as the ability to accurately place the seeds within the prostate has increased. Radioactive seed radiation therapy has the advantage of being relatively non-invasive, less costly, while complications and side effects are less common. A patient is able to leave the hospital/clinic shortly after treatment is completed, and can carry on with normal activities quite soon after.

Success of radiation seed therapy depends upon accurate placement of the radioactive seeds within the prostate. This is generally provided by a stepper assembly which moves an ultrasound probe in a highly controlled manner. The ultrasound probe, mounted on the stepper assembly, is positioned adjacent the prostate, in the rectum of the patient, and as the probe is stepped forward or to the rear, a different slice or plane of the prostate is displayed on the ultrasound monitor. This information is used by the operator to correctly position the radiation seeds in the prostate. The seeds are placed in the prostate by insertion needles which extend through a template mounted on the stepper assembly.

While the ultrasound probe can, with available stepper assemblies, be moved accurately in increments of a desired amount, there is no present capability of providing a known reference position for the successive stepping movement of the probe, apart from moving the entire stepper assembly on a separate mounting element to specifically locate the rear edge of the prostate. Movement of the entire assembly, unless the mounting element includes an expensive adjusting mechanism, can be cumbersome and not very accurate, typically only to within 2–3 millimeters.

It should be understood that, in addition to imaging and treatment of the prostate, stepper assemblies can be used in the imaging and treatment of other human internal organs.

It is thus desirable to have a stepper assembly which is capable of incremental movements of known distance for movement of the ultrasound probe and which is also capable of moving the probe in a continuous, controlled manner independent of the individual stepping movements, so as to provide a reference or base position for the succeeding indexed movements of the stepper and the probe.

DISCLOSURE OF THE INVENTION

Accordingly, the present invention is a stepper apparatus for holding and moving an ultrasound probe which is adapted for imaging/treatment of a human internal organ, the apparatus comprising: a support means for holding the ultrasound probe; first means for moving the probe support means longitudinally relative to the internal organ in indexed steps of known distance, such that successive images of the internal organ may be produced over the entire organ, wherein a rear edge of the organ typically cannot be located precisely by said first means; and second means interrelated with said first means for moving the probe support means substantially continuously longitudinally, such that a rear edge of the organ can be accurately determined and used as a precise reference point for subsequent indexed step movement of the probe support means.

BRIEF DESCRIPTION OF THE DRAWINGS

FIG. 4 is a longitudinal cross-section view of the stepper assembly of FIG. 1.

FIG. 5 is a lateral cross-section view of the stepper assembly of FIG. 1, taken along lines 5—5 in FIG. 4.

FIG. 6 is a partial cross-section view, taken along lines 6—6 in FIG. 5.

BEST MODE FOR CARRYING OUT THE INVENTION

Figure 1:
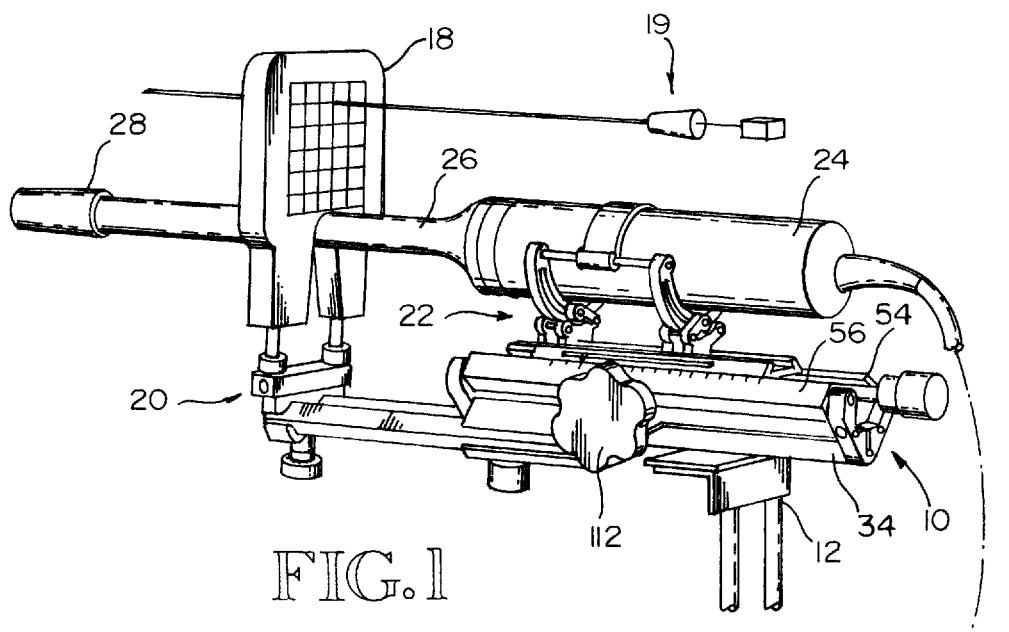
FIG. 1 is a perspective view showing the complete stepper assembly of the present invention.
Figure 2:
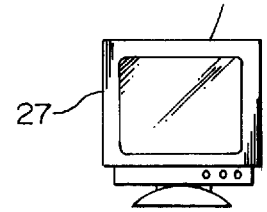
FIG. 2 is another perspective view of the stepper assembly of FIG. 1, without the probe.
Figure 2:
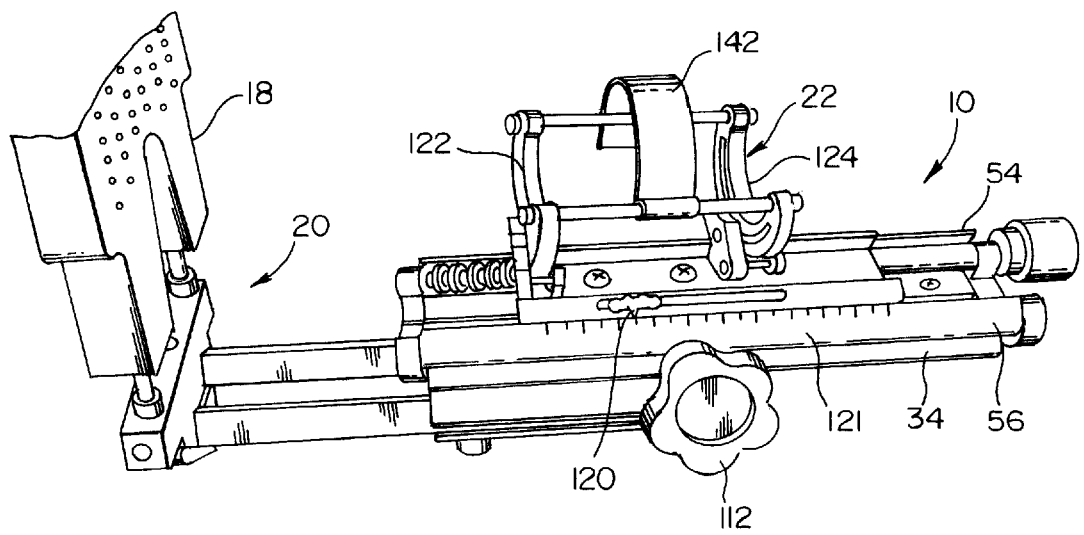

FIGS. 1 and 2 show the stepper assembly of the present invention, with FIG. 1 including an ultrasound probe 24. The stepper assembly is shown generally at 10, mounted on a support assembly 12 which in turn is connected to a support pad or plate (not shown) positioned on a treatment table upon which the patient reclines. The support pad is positioned beneath the patient, and the weight of the patient ensures the stability of the pad, the support assembly and the stepper assembly. The support assembly could also be secured directly to the table or the floor.

The stepper assembly 10 includes a vertically oriented needle guide or template 18 and template holder 20. FIG. 1 shows a single seed insertion needle 19 for illustration. The stepper assembly further includes an ultrasound probe holder 22. A conventional ultrasound probe 24 is positioned in and held by probe holder 22. Ultrasound probe 24 includes an elongated portion 26 with a conventional transmit/receive transducer element 28 located near the free end thereof. In operation, transducer element 28 is brought into proximity with the prostate via insertion in the rectal opening. As the probe is moved successive short distances by the stepper assembly, successive planar sections of the prostate are shown on an ultrasound monitor 27.

The physician in an initial imaging phase of the treatment moves the ultrasound probe by means of the stepper assembly in such a way as to develop an overall three-dimensional picture of the prostate. A pattern for placement of the radioactive seeds throughout the prostate is then developed in accordance with the initial scan and the configuration/location of the cancer. The seeds are then implanted in the prostate, with the guidance of the ultrasound display. Insertion needles with the seed loaded in them are inserted through the needle guide, into the perineum of the patient, and then into the prostate. The position of the needles is checked with the ultrasound display. These two phases are typically, but not necessarily, accomplished in two hospital/clinic visits. It may be possible to have the map prepared in real time following the scan, load the needles accordingly, and then insert the radioactive seeds into the prostate.

The stepper assembly 10 comprises several separate elements. The lowermost portion is a base or body portion 34. Body portion 34 is, in the embodiment shown, approximately 7 inches long and approximately 1.7 inches wide at its widest point. In cross-section, body portion 34 resembles an upside-down "W" with a rectangular channel 36 extending the length thereof. Two longitudinal, flat, spaced upper surfaces 38 and 40 border channel 36. Rectangular channel 36 is approximately 0.44 inches wide, while upper surfaces 38 and 40 are each approximately 0.34 inches wide. The end surfaces of the body portion have openings therein for attachment of end pieces 42 and 44, discussed in more detail below. Body portion 34 further includes side sections 46 and 48 which extend outwardly from the remainder of the body at an angle of 45° below the horizontal.

At the front end 35 of body 34 (closest to the template), side sections 46 and 48 are approximately 1.7 inches wide. At a distance of approximately 3.7 inches longitudinally from front end 35, the side sections decrease to zero in width such that from that point to the rear end of the body portion, it resembles a "v" in cross-section. In lower surface 50 of body portion 34 are threaded openings into which threaded elements (not shown) are positioned. The stepper assembly may be attached to a support assembly 12 of various configurations via the threaded elements.

Extending along and connected to each of the longitudinal upper surfaces 38 and 40 are skirt elements 54 and 56. The skirt elements are approximately 6.9 inches long and are approximately 0.75 inches wide. Each skirt includes three sections. A first horizontal section 58 is approximately 0.35 inches wide and includes spaced openings through which screws extend to secure the skirt to its associated upper surface of body portion 34. A second section 60 extends outwardly along an outer edge of the first section, at an angle of approximately 45° above the horizontal. The second section 60 is approximately 0.5 inches wide. The third section 64 extends inwardly at a 90° angle along an upper edge of the second section. The junctions between the first and second sections and the second and third sections are all radiused at a curvature of 0.06 inches.

Slide 66 is held between skirt elements 54 and 56. In the embodiment shown, slide 66 is approximately 4.5 inches long and 0.955 inches wide. Upper surface 68 of slide 66 is flat, while lower surface 70 is also flat, with the exception of a narrow channel 72 which extends the length of slide 66. In the embodiment shown, channel portion 72 is 0.312 inches wide and 0.04 inches deep. The sides of slide 66 are in the form of 90° V-shaped notches 74—74. Notches 74 extend from upper surface 68 of the slide to a point slightly above lower surface 70. In the embodiment shown, V-shaped notches 74 are approximately 0.180 inches deep at their deepest point.

Positioned in the notched side portions, respectively, of slide 66 are a longitudinal guide rod 78 and a threaded guide rod 80, on opposite sides of the slide. Guide rod 78 in the embodiment shown is 6.998 inches long and has a constant diameter along its length of 0.375 inches. At each end of guide rod 78 are end portions which fit into openings in end sections 42 and 44. Guide rod 80 is threaded in the embodiment shown for approximately 4.5 inches from a front end 81 thereof. In the embodiment shown, the threads have a 5 millimeter pitch with a 60° included angle. Each thread has a radius of 0.06 inches and is approximately 0.049 inches deep. Threaded rod 80 also has end portions which extend into end sections 42 and 44.

Mounted to upper surface 68 of slide 66 is a carriage 84. Carriage 84 in the embodiment shown is 4.5 inches long and 1.252 inches wide. Carriage 84 has a lower surface 86 and side surfaces 88 and 90 which extend outwardly in a 90° V-shape. Carriage 84 is approximately 0.330 inches at its highest points, which are near the side edges of the carriage. Extending down the middle of carriage 84 is a shallow channel 92. Channel 92 is approximately 0.75 inches wide and approximately 0.15 inches deep. Carriage 84 is mounted to slide 66 by threaded screws or the like through spaced openings in the carriage. Secured in channel 92 is probe holder 22, which will be discussed in more detail below.

Secured to the ends of body section 34 as indicated above are two end sections 42 and 44. End sections 42 and 44 are shaped somewhat like a "V" with a central vertical slot 96. In the embodiment shown, slot 96 is approximately 0.43 inches high and approximately 0.060 inches wide. End sections 42 and 44 are secured to body portion 34 by three screws 97—97 which extend through openings in the end section into the ends of body portion 34. A screw 98 extends laterally through the end section across slot 96. Turning screw 98 one way or the other will either draw the two portions laterally together (closing the slot to an extent) so as to slightly decrease the width of the end section, or permit the two portions to move slightly outwardly (opening the slot) slightly, increasing the width of the end section. This is used to tighten or loosen the fit of the guide rods relative to the slide, to accommodate wear, for instance. Access to the head of screw 98 is obtained by removal of the adjacent screw 97.

At the upper edges of each end section 42 and 44 are spaced openings 100 and 102. These openings accommodate the end portions of guide rod 78 and threaded rod 80. The very ends of guide rod 78 are flush with the outer surfaces of end sections 42 and 44, while a rear end portion 83 of threaded rod 80 extends beyond the outer surface of end section 44. In that rear end portion is a small depression 103 which receives a screw for holding on a knob 106. Knob 106 is used to turn the threaded rod 80.

Extending laterally through body portion 34, across channel 36, approximately longitudinally midway thereof, is a drive rod 110 with a knob 112 on one end thereof. Located on drive rod 110 in channel 36 is a gear 114. Gear 114 mates with a corresponding elongated rack element 116, attached to slide 66 in channel 72. Turning the knob 112 one way or the other will move slide 66 and carriage 84 mounted thereto longitudinally relative to body 34, which remains stably positioned.

Located in the side notch 74 of slide 66 adjacent the threaded rod 80 is a spring-loaded ball arrangement 118. The spring-loaded ball 118 and the slide 66 are configured and arranged such that the ball 118 fits into a thread of threaded rod 80, as shown in FIG. 6. It is the combined arrangement of threaded rod 80, spring-loaded ball 118 in the side notch 74 of slide 66, and the rack 116 and gear 114 which provides in this case an accurate stepping function, as well as an ability to move the slide and carriage continuously in a controlled, non-step fashion to determine an exact reference position for the carriage coincident with a true rear edge of the prostate, from which point the slide and carriage (with the probe) may then be stepped specific, known amounts, even the first step.

Turning threaded rod 80 in one direction or another by means of knob 106 will advance the slide and carriage in a continuous, non-stepped manner, with spring-loaded ball 118 riding in the threads of threaded rod 80. When the ultrasound picture on monitor 27 shows that the signal plane of the transmit/receive element 28 is precisely at the rear edge of the prostate, a movable reference indicator 120 on the side of the carriage is moved along a sliding track to line up with a zero or other reference indicia 121 printed along the side of skirt portion 56 (FIG. 2). Once this reference point has been established, with the reference indicator properly positioned, then rotation of knob 112 will produce successive 5 mm steps as the ball "jumps" from one thread of rod 80 to the next. Hence, with the embodiment shown, the stepper advances in 5 mm increments as the knob 112 is rotated and the ball moves from thread to thread.

The precise distance between successive threads in threaded rod 80 results in precise 5 mm movements of the stepper as knob 112 is rotated, moving the signal plane toward the front edge of the prostate. The physical relationship between the ball 118 and successive threads of the threaded rod 80, with the rack and gear arrangement permit the probe to be moved to a reference position and then moved in 5 mm increments from there, wherever that reference position is located.

In the embodiment shown, the desired step distance is 5 mm. The indicia 121 thus indicates 5 mm distances, and the threads of threaded rod 80 have a 5 mm pitch, with left hand thread. Again, in the embodiment shown the threads have a 60° included angle, with a 0.60 inch radius, 0.049 inches deep. If a different step distance is desired, then the indicia and the threaded portions must match the desired distance.

Hence, a significant advantage of the present invention is that in a relatively simple, but reliable, system, a precise reference or base plane can be established which is coincident with the back edge of the prostate, in combination with a stepping ability for the carriage and the ultrasound probe of movement in accurate 5 mm increments from the reference point, so that the entire prostate can be accurately viewed in successive 5 mm planes. Again, the stepper apparatus could be used for imaging/treatment of other internal organs and with other stepping distances.

An alternative structure could use the same rack/gear arrangement, with two non-threaded guide rods, with one rod having detents at 5 mm increments. Indexed movement can be obtained as the slide is moved by the rack/gear because the ball on the side surface of the slide moves between detents on the rod. Continuous movement can be obtained by rotating the one rod such that the ball does not move between detents, and then simply rotating the lateral drive rod, moving the slide via the rack and gear arrangement. The other rod could have other increments on it, such as 1 mm. In this embodiment, however, a truly movable reference point is not possible, as the first indexed movement will be an unknown distance when the rod with the detents is moved back into alignment with the movement of the ball.

Figure 3:
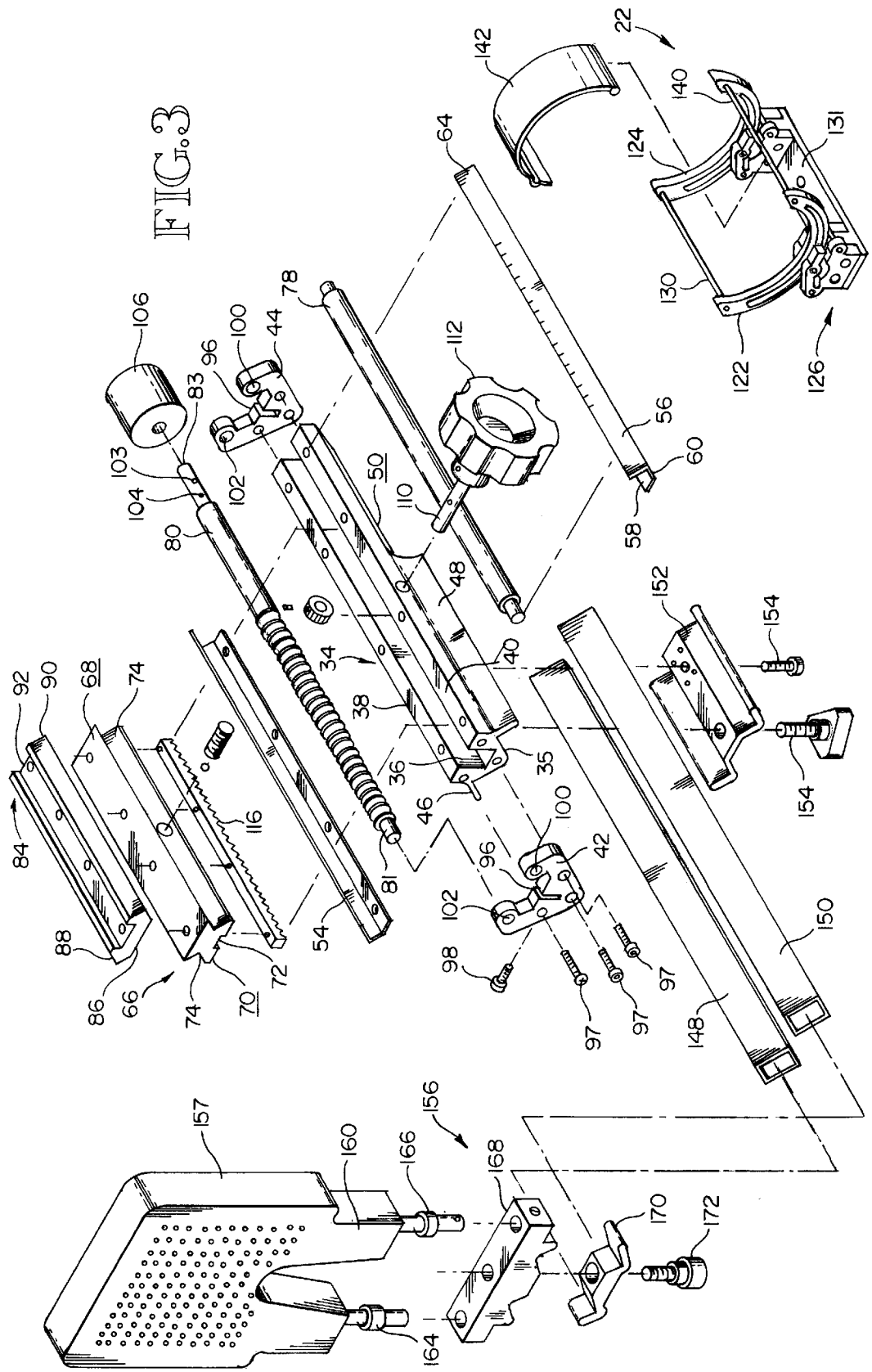
FIG. 3 is an exploded view of the stepper assembly of FIG. 1.

Referring again to the embodiment of FIG. 3, it may be suitable in some cases to have step distances of less than 5 mm while retaining the 5 mm step capability. This can be accommodated by a modification of the arrangement shown. A spring-loaded ball arrangement can be positioned in end section 44 so that the ball extends slightly into opening 102 in the end section. The ball mates with circumferential detents 104 on the surface of end portion 83 of threaded rod 80, at 72° increments. Each click of the knob 106 will result in a longitudinal movement of the probe of one degree. Other distances can be readily accomplished. This 1 mm step capability can be readily eliminated (so that continuous movement is again possible) by simply backing off the screw (not shown) holding the spring-loaded ball in place, allowing threaded rod 80 to be turned freely and continuously by knob 106.

The probe holder is shown in FIGS. 2–5. Two probe cradles 122 and 124 are each mounted to a pair of support pieces 126 (exterior) and 128 (interior). Support pieces 126 and 128 are each in turn mounted to a support plate 131 which is mounted to an upper surface of carriage 84 in channel 92. Each support piece 126, 128 (FIG. 5) is approximately 0.188 inch thick, and includes an arm-like section 129 which is secured at one end thereof to the body 130 of the support piece. Arm 129 is thus free to move slightly toward and away from body 130 about its attachment to body 130.

Extending between each pair of support pieces 126, 128 are two spaced roller rods 132—132, as well as a holder rod 134. Each cradle 122, 124 is positioned between its associated pair of support pieces. Cradle 122, which is identical to cradle 124, is in the form of a ring portion, approximately 0.185 inches thick, with an outer radius of 1.228 inches and an inner radius of 0.908 inches. Extending through the ring portion, along substantially its entire length, is a slot 136. Holder rod 134 extends between the two support pieces 126 and 128 through slot 136. The lower edge of cradle 122 rests on the surfaces of roller rods 132. Hence, cradle 122, along with the ultrasound probe which is positioned therein, as explained below, can be rotated by rotating the cradle about holder rod 134.

Extending between the respective free ends of the two spaced cradles 122 and 124 are two cradle rods 138 and 140. A thin probe holder 142 is rotationally secured to one cradle rod 140 and snaps onto the other cradle rod 138. The probe holder 142 secures the ultrasound probe 24 into position against the upper edges of cradles 122 and 124. Again as indicated above, the ultrasound probe can be rotated by rotating the cradles.

The template and template holder structure are also shown in detail in FIG. 3. Extending longitudinally forwardly from the lower surface of body 34 are two template support rods 148 and 150. In the embodiment shown, rods 148, 150 are approximately 6.62 inches long and are square in cross-section. They are arranged to nest with the configuration of the lower surface of body portion 34. Holding the template rods 148, 150 to the lower surface of body 34 is a clamp 152. Screws 154—154 extend through clamp 152 into body 34, firmly holding the template rods 148 and 150 between the clamp and the body. One of the screws has a knob on the end thereof which permits convenient loosening of the clamp so that the rods can slide in and out longitudinally.

Clamped to the free ends of template rods 148, 150 is the needle guide template assembly 156. Template assembly 156 includes a guide template 157. Template 157 is a conventional template for seed insertion needles, comprising a pattern of columns and rows of needle openings. In the embodiment shown, there are 13 rows and 13 columns of openings. Template 157 is large enough to accommodate the cross section of virtually all prostates. In the embodiment shown, template 157 is approximately 3½ inches wide and 3¼ inches high in its main section. Two support leg sections 158, 160 extend downwardly from a lower edge of the main portion of the template 157. Extending from leg portions 158, 160 are two holder elements 164 and 166 which fit into mating openings in a template holder 168. Template 157 and holder 168 are supported and secured to the template rods 148 and 150 by a template clamp 170 and bolt 172.

In use the conventional ultrasound probe is held by cradle elements 122 and 124. The elongated front end of the ultrasound probe extends through the opening between the leg portions 158 and 160 of the template. In the imaging/treatment of the prostate, the patient is situated on the table, lying on the support pad, such that the entire stepper assembly is securely positioned, and the ultrasound probe is positioned such that the tip of the ultrasound probe is positioned into the body of the patient so that it is approximately adjacent the prostate. The ultrasound apparatus is then activated, providing a picture of the prostate along a given plane. Knob 106 is then rotated, moving the slideable carriage 84 and probe 24 to the point where the plane of the ultrasound signal is coincident with the very rear edge of the prostate. The reference indicator 120 is then moved to a reference mark of indicia 121.

The slide carriage and probe may then be stepped in 5 mm increments by turning knob 112, covering the entire length of the prostate. Hence a complete "map" of the prostate results, in successive longitudinal increments of 5 mm. The pattern or map of the placement of the radiation seeds at 5 mm increments will then be developed, in accordance with the extent of the cancer. The resulting positioning of the radioactive seeds can be very accurate because of the known reference position of the stepper assembly. This has the advantage of providing the best, most effective coverage for the radiation produced by the seeds in the prostate.

After the mapping of the placement of the radiation seeds is accomplished, a first insertion needle is inserted through an opening in the guide template. The insertion needle includes an outer sleeve (catheter-like) and an inner solid stylet element. The radiation seeds are positioned within the outer sleeve, spaced in order according to their desired position within the prostate, spaced apart with spacer elements. Using the ultrasound monitor, the individual needles are then inserted through the skin and surface tissues (perineum) of the patient to the prostate region. The end of the outer sleeve is located at the rear edge of the prostate.

The seeds are deposited by sliding the outer sleeve rearwardly along the inner sleeve, leaving the seeds in the desired position in the prostate. The first needle is withdrawn and the next "loaded" needle inserted. This process continues until all the desired seeds have been put into place in the prostate. Once this is completed, the probe is removed, and the patient is free to leave. As indicated above, the procedure is usually carried out in two steps, at two different times, one for the initial imaging and then one for the actual treatment. However, it is possible that the entire process could be carried out at one time.

While there is certainly some discomfort, the process is done on an out-patient basis and recovery is typically quite rapid, usually without any significant side effects or other complications. The accurate positioning of the radiation seeds has been shown to be quite effective in the treatment of cancers of the prostate.

Accordingly, the present invention provides a capability of providing both the required accurate stepping of the carriage and the ultrasound probe but also the convenient and accurate determination of a reference position for the stepper assembly coincident with the rear edge of the prostate.

Although a preferred embodiment of the invention has been disclosed herein for illustration, it should be understood that various changes, modifications and substitutions may be incorporated in such embodiment without departing from the spirit of the invention, which is defined by the claims as follows:

What is claimed is:

1. A stepper apparatus for holding and moving an ultrasound probe which is adapted for imaging/treatment of a human internal organ, the apparatus comprising:

a support means for holding the ultrasound probe;

first means for moving the probe support means longitudinally relative to the internal organ in indexed steps of known, preselected distance, such that successive cross-sectional images separated by said preselected distance of the internal organ may be produced for the entire organ, wherein a rear edge of the organ typically cannot be located precisely by said first means; and second means interrelated with but separately operable from said first means for moving the probe support means substantially continuously longitudinally, such that a rear edge of the organ can be accurately determined and used as a precise reference point for subsequent indexed step movements of the probe support means, wherein initial and subsequent steps from the reference point produced by the first means are for said preselected distance.

2. An apparatus of claim 1, wherein the internal organ is the prostate and the apparatus includes a support means for holding a template having a plurality of openings therethrough through which insertion needles containing radioactive seeds for placement by the apparatus in desired position in the prostate may be positioned.

3. An apparatus of claim 1, wherein the first and second moving means includes a sliding assembly which moves along two spaced longitudinal rod-like support elements, one rod including a threaded portion, wherein the sliding assembly including a movable element which rides in the threads of the threaded portion of the one rod, the threaded rod includes means for turning said rod so that the sliding assembly and the probe moves continuously longitudinally when the rod is turned.

4. An apparatus of claim 3, wherein the sliding assembly includes a rack and mating gear arrangement, the rack being mounted on the sliding assembly, wherein the distance between adjacent threads on the threaded portion of said one rod is a selected distance so that as the gear is turned, the movable element moves between adjacent threads, providing successive movements of the probe equal to the distance between successive threads.

5. An apparatus of claim 4, wherein the movable element is a spring-loaded ball in the side of the sliding assembly, and wherein the rack and gear arrangement includes a drive rod on which the gear is mounted and means located on the rod to turn the gear.

6. An apparatus of claim 1, including an adjustable reference pointer member on the sliding assembly which can be moved to mate with a reference indicia on a fixedly positioned base portion of the stepper apparatus.

7. An apparatus of claim 4, including a base portion, two end portions for supporting the longitudinal guide rods, two skirt-like elements mounted on and extending along an upper surface of the base position at opposing edges thereof, the skirt-like elements extending around an outer portion of the guide rods, wherein the sliding assembly includes a slide element having the rack mounted to a lower surface thereof, the stepper assembly further including a carriage portion mounted to an upper surface of the slide element for directly supporting the probe holder.

8. An apparatus of claim 7, wherein the end portions have a vertical slot therein, defining two parts of each end portion, and means extending across the slot, into each said part, for moving the two parts slightly closer together, thereby moving the guide rods slightly closer together.

9. An apparatus of claim 1, wherein the ultrasound probe support means includes two spaced support assemblies and a cradle assembly supported therebetween for holding the ultrasound probe, wherein the cradle assembly is supported in such a manner that the cradle assembly and the ultrasound probe can be rotated through a desired angle.

* * * * *